(12) United States Patent
Abt et al.

(10) Patent No.: US 11,246,752 B2
(45) Date of Patent: Feb. 15, 2022

(54) SURGICAL TOOL ATTACHMENT SYSTEMS AND METHOD OF USE

(71) Applicant: NOVARTIS AG, Basel (CH)

(72) Inventors: Niels Alexander Abt, Winterthur (CH); Thomas Linsi, Schaffhausen (CH)

(73) Assignee: Alcon Inc., Rue Louis-d'affry (*) Notice: Subject to any disclaimer, the term of this patent is extended or adjusted under 35 U.S.C. 154(b) by 502 days.

(21) Appl. No.: 16/249,035

(22) Filed: Jan. 16, 2019

(65) Prior Publication Data

US 2019/0247229 A1    Aug. 15, 2019

Related U.S. Application Data

(60) Provisional application No. 62/628,918, filed on Feb. 9, 2018.

(51) Int. Cl.
  *A61F 9/007* (2006.01)
  *A61B 17/29* (2006.01)
  *A61B 17/30* (2006.01)

(52) U.S. Cl.
  CPC ...... *A61F 9/00727* (2013.01); *A61B 17/2909* (2013.01); *A61F 9/00736* (2013.01); *A61B 2017/2929* (2013.01); *A61B 2017/2946* (2013.01); *A61B 2017/305* (2013.01)

(58) Field of Classification Search
  CPC ............. A61F 9/00727; A61F 9/00736; A61B 17/2909; A61B 2017/2929; A61B 2017/2946; A61B 2017/305
  See application file for complete search history.

(56) References Cited

U.S. PATENT DOCUMENTS

| | | |
|---|---|---|
| 6,855,156 B2 | 2/2005 | Etter |
| 6,908,476 B2 | 6/2005 | Jud |
| 6,945,984 B2 | 9/2005 | Arumi |
| 9,795,505 B2 | 10/2017 | Yu |
| 9,827,141 B2 | 11/2017 | Schaller |
| 10,045,883 B2 | 8/2018 | Egli |
| 2007/0287993 A1 | 12/2007 | Hinman |

(Continued)

FOREIGN PATENT DOCUMENTS

| | | |
|---|---|---|
| DE | 102011053517 A1 | 3/2013 |
| WO | WO0230302 A1 | 4/2002 |

OTHER PUBLICATIONS

Grieshaber Catalog (2011), 2 pages.

(Continued)

*Primary Examiner* — Diane D Yabut

(57) ABSTRACT

The present disclosure describes systems and methods for selectively constraining an orientation of a portion of a surgical tool system relative to another. Example surgical tool systems may include a surgical tool having at least one movable component, at least one actuation component, and a surgical tool attachment. The surgical tool attachment may be operable selectively to engage and disengage the moveable component so as to prevent movement of the movable component relative to the surgical tool in an engaged configuration and to permit movement of the movable component relative to the surgical to in a disengaged configuration, respectively. In the engaged configuration, a dynamic component of the surgical tool system may be fixed relative to the surgical tool, and, in a disengaged configuration, the dynamic component may be freely movable relative to the surgical tool.

7 Claims, 6 Drawing Sheets

(56) References Cited

U.S. PATENT DOCUMENTS

| | | |
|---|---|---|
| 2014/0135820 A1 | 5/2014 | Schaller |
| 2014/0277046 A1 | 9/2014 | Mark |
| 2015/0173944 A1 | 6/2015 | Linsi |
| 2017/0281295 A1 | 10/2017 | Abt |
| 2017/0296382 A1 | 10/2017 | Mukai |

OTHER PUBLICATIONS

Guven, et al., "Implantation of an inactive epiretical poly (dimethyl siloxane) electrode array in dogs," May 23, 2005, Experimental Eye Research 82 (2006) 81-90.

Grieshaber & Co., AG, "The Greishaber Retinal Tacks," Aug. 1998, 2 pages.

Alcon Grieshaber AG, "Microinstruments and Handles, Quick Lock Connector Tips," Oct. 2008, 4 pages.

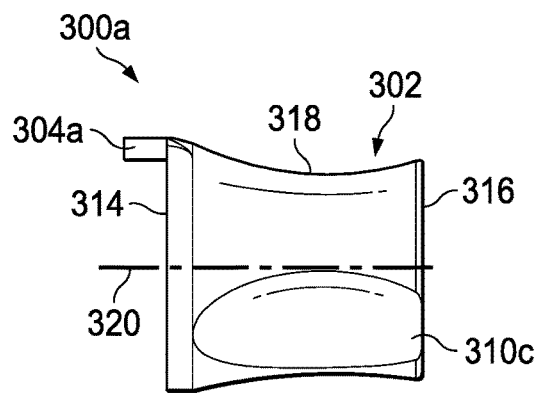
FIG. 4D
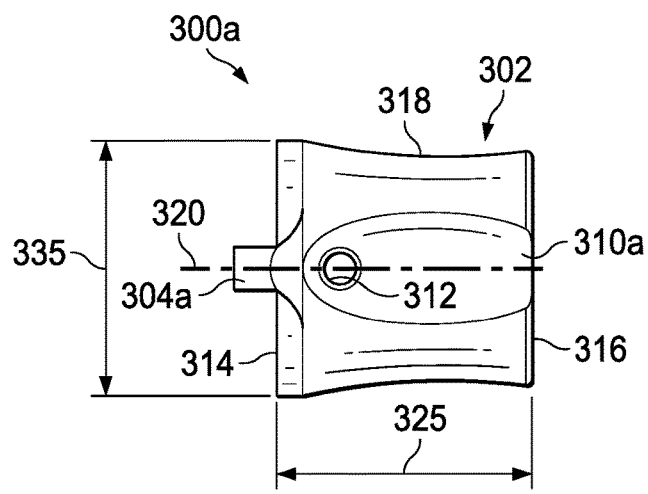 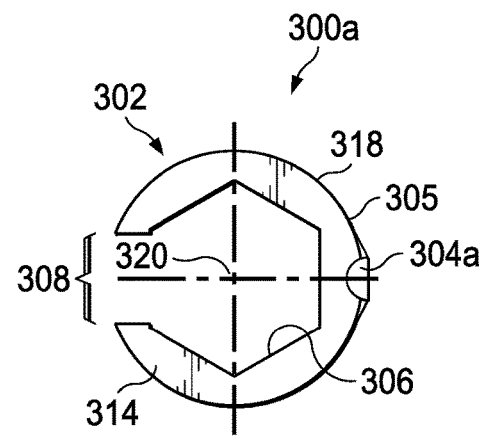
FIG. 4A
FIG. 4B
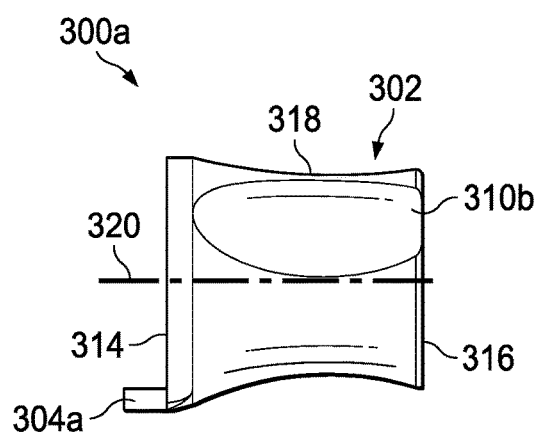
FIG. 4C

SURGICAL TOOL ATTACHMENT SYSTEMS AND METHOD OF USE

CROSS-REFERENCE TO RELATED APPLICATIONS

This application claims the benefit of U.S. Provisional Application No. 62/628,918, filed Feb. 9, 2018, the entire contents of which is incorporated herein by reference in its entirety.

TECHNICAL FIELD

The present disclosure relates to ophthalmic surgery and surgical equipment, and more specifically, to ophthalmic surgical tool systems, attachments, and methods of use.

BACKGROUND

Ophthalmic surgery is performed on the eye to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in precision or accuracy of surgical techniques can make a tremendous difference in the patient's vision after the surgery.

In certain ophthalmic surgeries, interior portions of the eye are cut, grasped, removed, or repaired using miniaturized instruments, often referred to as micro-surgical tools. Such tools may contain mechanically actuated components that act upon the eye. For instance, micro-surgical tools may include forceps, shears, and scissors. Precise positioning of these tools allows for their accurate use and improves patient outcomes, but precise positioning can be difficult to maintain when movable components of these tools are not immobilized.

SUMMARY

A first aspect of the present disclosure may include a surgical tool system that may include a surgical tool and a surgical tool attachment configured to be coupled to the surgical tool. The surgical tool may include a handle portion configured to be grasped by a hand of a user; at least one movable component; and at least one actuation component. The surgical tool attachment may include a body that may include a tab extending from a first end of the body and operable to interfere with the at least one movable component of the surgical tool; a cavity extending longitudinally through the body and configured to be slidably receive the surgical tool; and a slot extending radially outwards from the cavity through an entirety a side of the body and extending at least partially along a length of the body so as to not interfere with the at least one actuation component of the surgical tool.

According to another aspect, the disclosure describes a surgical tool attachment that may include a body operable to be coupled to a surgical tool. The body may include a cavity extending longitudinally through the body configured to receive the surgical tool and a slot extending radially outwards from the cavity through an entirety of a side of the body. The cavity may extend at least partially along a length of the body. The surgical tool attachment may also include a tab extending lengthwise from a first end of the body and operable to interfere with a movable component of the surgical tool.

According to another aspect, the disclosure describes a method of configuring a surgical tool system. The method may include determining a first configuration of the surgical tool system; adjusting a movable component of a surgical tool into a first orientation corresponding to the first configuration; and positioning the surgical tool attachment into a first position corresponding to the first configuration such that the surgical tool attachment secures the movable component in the first orientation.

The various aspects may include one or more of the following features. The surgical tool attachment may be integrated into the surgical tool. The tab may be disposed on an outer edge of the body. The cavity may include a cross-sectional shape that corresponds to a cross-sectional shape of the surgical tool. The cross-sectional shape of the cavity may be hexagonal. The surgical tool attachment may also include at least one depression formed in an exterior surface of the body. The exterior surface of the body may form an ergonomic gripping surface to the hand of the user. The at least one movable component may include a plurality of notches. The tab may include a cross-sectional shape that corresponds to a cross-sectional shape of the notches. The tab may be configured to be insertable into at least one of the notches so as to secure the at least one movable component in an orientation with respect to the surgical tool. The at least one movable component may include a plurality of raised portions. The tab may include a cross-sectional shape that defines a channel that is configured to receive at least one of the raised portions of the at least one movable components so as to secure the at least one movable component in an orientation with respect to the surgical tool. The surgical tool attachment may also include an aperture formed in the body and extending from the cavity to an exterior of the body.

The various aspects may also include one or more of the following features. A body of a surgical tool attachment may be coupled to a surgical tool. The body may include a cavity extending longitudinally through the body configured to receive the surgical tool and a slot extending radially outwards from the cavity through an entirety of a side of the body and extending at least partially along a length of the body. The surgical attachment tool may also include a tab extending lengthwise from a first end of the body and operable to interfere with a movable component of the surgical tool. The cavity may include a cross-sectional shape that is configured to correspond to a cross-sectional shape of the surgical tool. The cross-sectional shape of the cavity may be hexagonal. At least one depression may be formed in an exterior surface of the body so at to form the exterior surface of the body that provides an ergonomic gripping surface to a hand of a user. The tab may have a cross-section configured to conform to a feature formed on the movable component of the surgical tool.

A method of configuring a surgical tool system may also include determining second configuration for the surgical tool system; positioning the surgical tool attachment into an intermediate position such that the surgical tool attachment does not prevent the movable component from moving; adjusting the movable component of the surgical tool into a second orientation corresponding to the second configuration; and positioning the surgical tool attachment into a second position corresponding to the second configuration such that the surgical tool attachment secures the movable component in the second orientation. A method of configuring a surgical tool system may also include coupling the surgical tool attachment to the surgical tool. Coupling the surgical tool attachment to the surgical tool may include aligning a cavity in the surgical tool attachment with a first end of the surgical tool and sliding the surgical tool attachment along the surgical instrument toward a second end of the surgical tool opposite the first end. Positioning the surgical tool attachment into a first position may also include positioning the surgical tool attachment at a position adjacent to the movable component of the surgical tool; aligning a tab of the surgical tool attachment with a notch formed in the movable component; and inserting the tab into the notch of the movable component such that the tab interferes with the movable component and secures the movable component in the first orientation.

Any of the above systems may be operated using any of the above methods and any of the above methods may be applied to any of the above systems. It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description

BRIEF DESCRIPTION OF THE DRAWINGS

For a more complete understanding of the present disclosure and the associated features and advantages described herein, reference is now made to the following description, taken in conjunction with the accompanying drawings, which are not to scale, in which like numerals refer to like features, and in which:

FIGS. 4A, 4B, 4C, and 4D are various views of an example surgical tool attachment.

DETAILED DESCRIPTION

Figure 1:
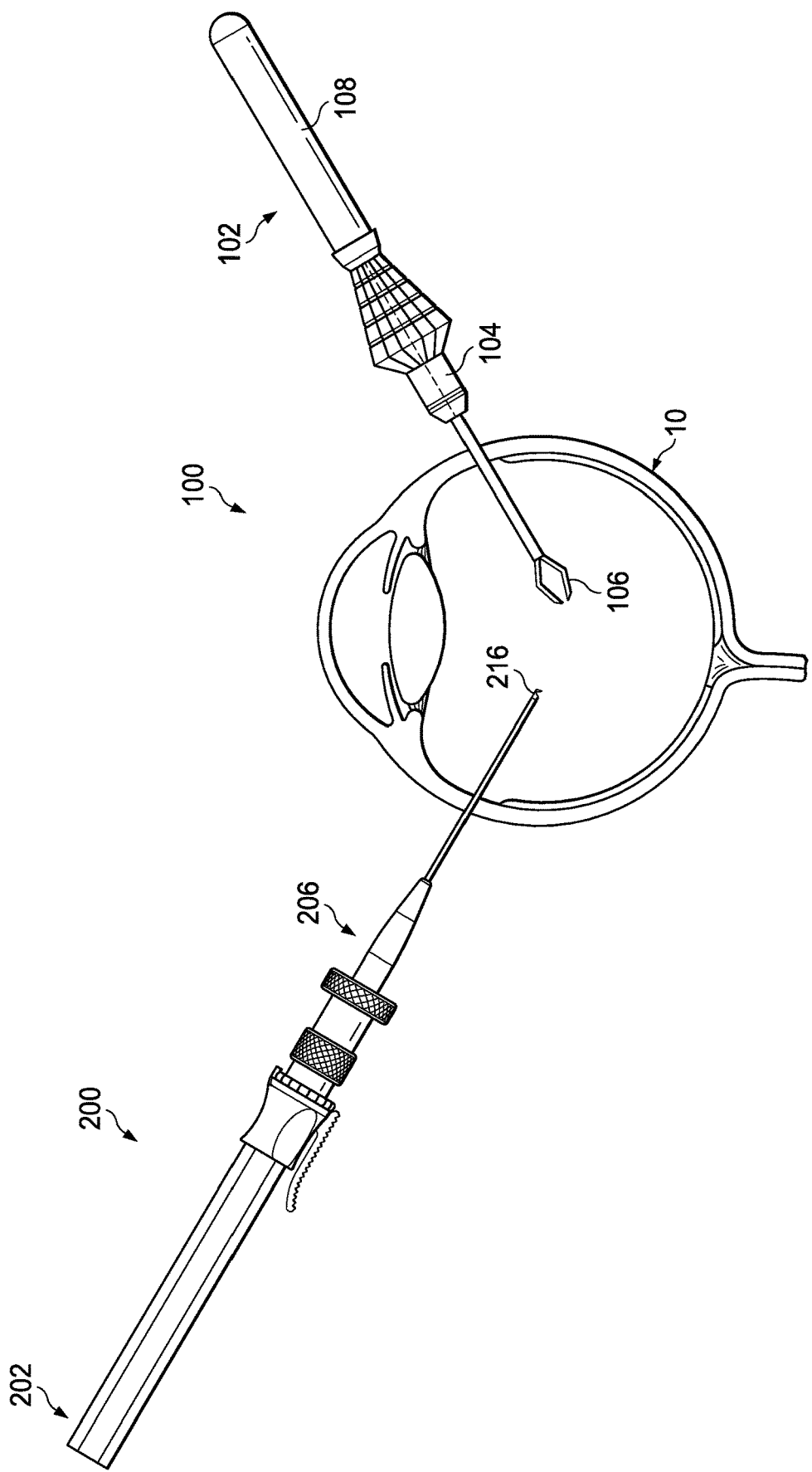
FIG. 1 shows an example system for ophthalmic surgery.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. Further, the method steps described herein may be used in any combination and may performed in any order unless clearly mutually exclusive.

The disclosed surgical tool systems and methods of use may improve precise positioning of surgical tools, particularly those with movable components located on the surgical tool that adjust the orientation of a surgical tool tip, by providing for a surgical tool attachment that immobilizes a movable component of the surgical tool, and, thereby, secures the tool tip in a given orientation with respect to the surgical tool. This avoids or greatly reduces inadvertent changes in the orientation of the movable component and the tool tip that sometimes occurs when positioning, actuating, or otherwise using the surgical tool. These inadvertent changes in orientation may often result from coupled actuation and positioning, hand fatigue, intention tremor, and other inadvertent hand movements. Using a system or method of the present disclosure, inadvertent movements, such as, for example, actuation effects, hand fatigue, and other inadvertent hand movements, do not change the orientation of the movable component and the tool tip. As a result, negative effects, e.g., inadvertent changes in orientation, are avoided or minimized.

Systems of the present disclosure typically include a surgical tool and a surgical tool attachment. In some implementations, the surgical tool attachment may be attached to the surgical tool by coupling the surgical tool attachment over a distal end of the surgical tool. For example, in some instances, the surgical tool attachment may be slid over a distal end of the surgical tool in order to couple the surgical tool attachment to the surgical tool. However, other attachment designs and methods of attaching the surgical tool attachment to the surgical tool are encompassed within the present disclosure. The surgical tool attachment prevents rotation of the surgical tool attachment relative to the surgical tool and temporarily immobilizes a movable component of the surgical tool. Example systems and components are described in greater detail in FIG. 1 through FIG. 6. However, aspects of these systems and components may be combined with one another and with systems and components otherwise described herein, but not illustrated in the figures.

FIG. 1 illustrates an example system 100 for ophthalmic surgery. The system 100 includes a first surgical tool system 200 and second surgical tool system 102. As shown in FIG. 1, the first surgical tool system 200 includes a tool tip 206 and the second surgical tool system 102 includes a tool tip 104. The tool tip 206 and the tool tip 104 are illustrated as being disposed, at least partially, in a patient's eye 10 (the patient's eye 10 is depicted to better illustrate how the systems may be used, but is not a component of any system). The tool tip 206 and the tool tip 104 may include a dynamic component 216 and a dynamic component 106, respectively. The dynamic component 216 and the dynamic component 106 move within the patient's eye 10 when actuated. For instance, the dynamic component 216 may include forceps, such as the Sutherland "Tack" Microforceps depicted in FIG. 1 and produced by Alcon Laboratories, Inc., located at 6201 South Freeway, Fort Worth, Tex. 76134 (referred to hereinafter as "Tack Microforceps"). The Tack Microforceps is used to insert tacks that hold the retina against the back of the eye. In other instances, the dynamic component 216 may include internal limiting membrane (ILM) forceps, end-grasping forceps, asymmetrical forceps, fiber optic forceps, or microtextured forceps, such as MAX GRIP® forceps produced by Alcon Laboratories, Inc., located at 6201 South Freeway, Fort Worth, Tex. 76134. The dynamic component 216 may also include scissors, such as curved scissors or vertical scissors. The dynamic component 216 may further include shears. The dynamic component 106 is depicted in FIG. 1 as forceps. However, the dynamic component 106 may be other types of components, such as any of the components listed with reference to the dynamic component 216. Moreover, the scope of the disclosure is not so limited, and the dynamic component 216 and the dynamic component 106 are intended to encompass other types of mechanisms, tools, or instruments for use within a surgical procedure.

With continued reference to FIG. 1, the first surgical tool system 200 also includes a surgical tool 202, which may be similar to a Sutherland handle such as the GRIESHABER SUTHERLAND NG handle produced by Alcon Laboratories, Inc., located at 6201 South Freeway, Fort Worth, Tex. 76134. The first surgical tool system 200 and the surgical tool 202 thereof are described in more detail below with respect to FIG. 2. As depicted in FIG. 1, the second surgical tool system 102 includes a surgical tool 108, which may be similar to the GRIESHABER REVOLUTION® handle, the GRIESHABER REVOLUTION® DSP handle, or the handles described in U.S. Pat. Nos. 6,482,198 and 6,488,695, both of which are incorporated by reference herein. In other implementations, the surgical tool 108 may be similar to the GRIESHABER® RENAISSANCE® handle or the handles described in U.S. Pat. No. 6,908,476, which is incorporated by reference herein. In still other implementations, the surgical tool 108 may be similar to the surgical tool 202, and thus, similar to a Sutherland handle such as the GRIESHABER SUTHERLAND NG handle described above. In some implementations, the surgical tool system 102 may include a light source or an illuminator. However, the scope of the disclosure is not so limited. Rather, the handles and tools described above are provided merely as examples. Consequently, the surgical tool 202 and the surgical tool 108 are intended to encompass other types of surgical tools, handles, or instruments for use within a surgical procedure.

The tool tip 206, the tool tip 104, and any components thereof, such as the dynamic component 216 or the dynamic component 106, may be integrally formed with the surgical tool system 200 or the surgical tool system 102. In other implementations, the tool tip 206, the tool tip 104, and the associated components thereof may be removable and even replaceable with respect to the surgical tool system 200 and the surgical tool system 102.

In some implementations, the tool tip 206, the tool tip 104, and/or other portions thereof (e.g., the portions of the tool tips inserted into the eye 10) may have a gauge size of 20 gauge, 23 gauge, 25 gauge, or 27 gauge. However, the scope of the disclosure is not so limited. Rather, the size of the tool tip 206, the tool tip 104, and/or any component thereof may have any desired and suitable size.

As depicted in FIG. 1, the system 100 may be used to perform an ophthalmic surgical procedure. For example, the system 100 may be used to repair a giant retinal tear. As shown in FIG. 1, the surgical tool system 200 includes the surgical tool 202 (which, as explained above, may be similar to a Sutherland handle in some instances), the tool tip 206, and the dynamic component 216. In some instances, the dynamic component 216 may be similar to the Tack Microforceps, as described above. The tool tip 206 and the dynamic component 216 may be actuated such that dynamic component 216 is made to grasp an item, such as a feature of the eye or another surgical device. For example, in some instances, the dynamic component 216 may be actuated to manipulate a retinal tack (not expressly shown). The surgical tool system 200 may be used to position and insert the retinal tack within the patient's eye 10 to secure a part of a detached retina and, thereby, repair a giant retinal tear. However, the scope of the disclosure is not so limited. The system 100 is intended to encompass other systems, including other surgical instruments and equipment for use within other surgical procedures.

Figure 2:
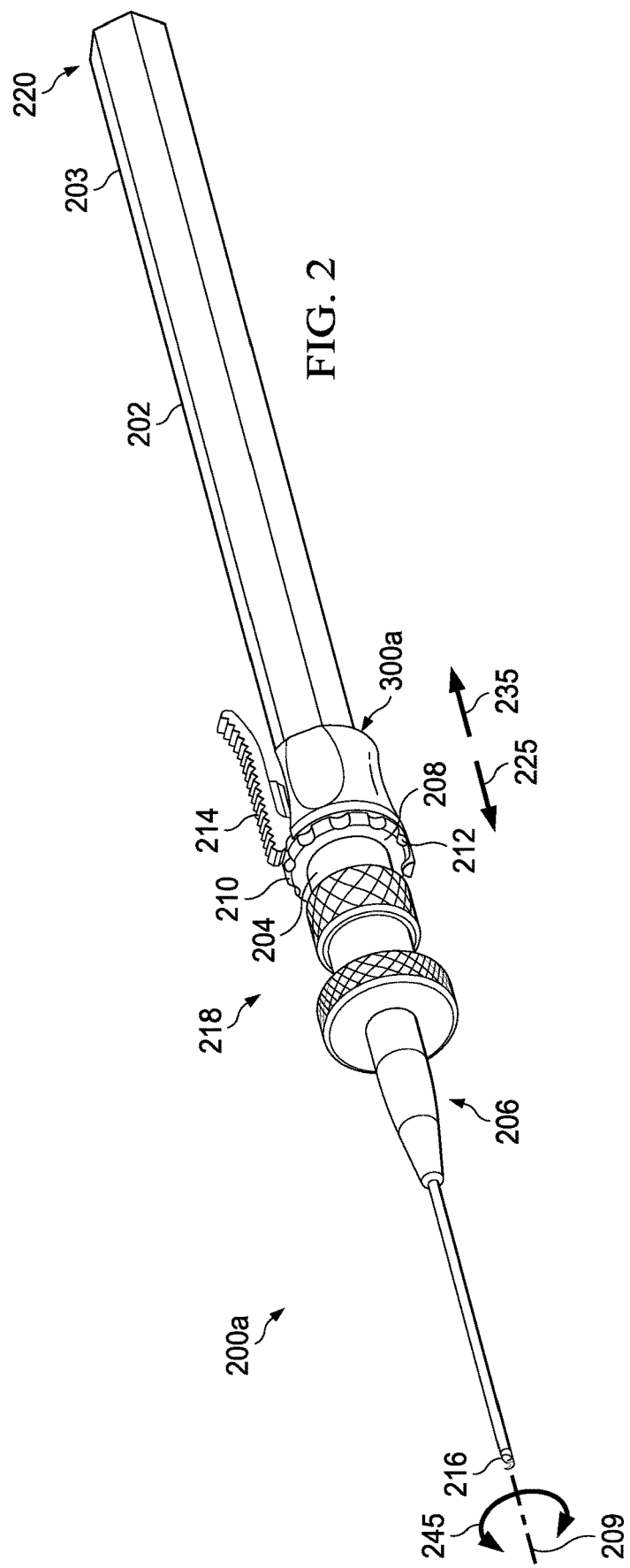
FIG. 2 is a perspective view of an example surgical tool system with an example surgical tool attachment and a surgical tool similar to a GRIESHABER SUTHERLAND NG handle produced by Alcon Laboratories, Inc., located at 6201 South Freeway, Fort Worth, Tex. 76134.

FIG. 2 illustrates an example surgical tool system 200a with an example surgical tool attachment 300a (described in more detail below), and a surgical tool 202. In some instances, the surgical tool 202 may similar to a GRIESHABER SUTHERLAND NG handle described previously. As described above, the surgical tool 202 may also encompass other types of surgical tools, handles, or instruments for use within a surgical procedure. The surgical tool 202 includes a handle portion 203 configured to be grasped by the hand of a user; an actuation component operable to actuate the dynamic component 216 of the tool tip 206; and a movable component operable to rotate the tool tip 206 about the longitudinal axis 209 relative to the handle portion 203 and the actuation component. In some implementations, the actuation component may be fixed relative to the handle portion 203 about the longitudinal axis 209. In the illustrated example, the actuation component is an actuation lever 214 that is pivotable radially relative to the handle portion 203 and may be actuated by a finger or another portion of a user's hand. Particularly, in the illustrated example, the actuation lever 214 is pivotable about an axis that is perpendicular to the longitudinal axis 209. Also, in the illustrated example of FIG. 1, the movable component is in the form of a rotatable disc 208 that is rotatable about the longitudinal axis 209.

The surgical tool system 200a also includes a tool tip 206. The tool tip 206 is positioned on or attached to the surgical tool 202 at a distal end 218 thereof. In some instances, the tool tip 206 may be permanently attached to the surgical tool 202. In other instances, the tool tip 206 may be removable and replaceable with a replacement tool tip 206 or some other attachable and detachable tool. In those implementations where the tool tip 206 is removable and/or replaceable, the surgical tool 202 may include a tool tip coupler 204 located at the distal end 218 of the surgical tool 202. The tool tip 206 couples to the surgical tool 202 at the tool tip coupler 204. In those implementations where the tool tip 206 is integrally formed with the surgical tool 202, the tool tip coupler 204 may be omitted.

In the example shown in FIG. 2, the surgical tool 202 includes an actuation component that is in the form of the actuation lever 214, as explained above. The manipulation of the actuation lever 14 by a user (e.g., a surgeon or other medical professional) causes actuation of the dynamic component 216. Although the actuation lever 14 is shown, other types of actuation components or mechanisms may be employed to cause actuation of the dynamic component 216. For example, a rotary actuator, a sliding actuator, or some other type of actuator may be incorporated into the surgical tool 202 to permit a user to actuate the dynamic component 216.

For the purpose of the example shown in FIG. 2, the operation of the surgical tool system 200a is explained in the context of a Tack Microforceps. However, as explained above, the scope of the present disclosure is not so limited. As depicted in FIG. 2, the actuation lever 214 may be depressed by a first hand of a user to extend the Tack Microforceps included in the dynamic component 216. The Tack Microforceps may then be used to engage the retinal tack, and the actuation lever 214 may be released to retract the Tack Microforceps and secure the retinal tack by the dynamic component 216. After the user positions and inserts the retinal tack within the patient's eye 10, the actuation lever 214 may be depressed again to extend the Tack Microforceps and disengage the retinal tack. As described above, the dynamic component 216 may include other instruments, and the actuation lever 214 may be used to actuate these different types of instruments. For example, the actuation lever 214 may be operated to actuate scissors, shears, or other forceps to cut, grasp, or otherwise manipulate tissue or other structures within the patient's eye 10.

As explained above, the example surgical tool 202 includes a movable component that is in the form of the rotatable disc 208. However, the scope of the disclosure is not so limited, and the movable component may take on other forms that allow for adjusting a rotational orientation of the tool tip 206 about longitudinal axis 209 of the surgical tool 202 relative to the handle portion 203. As illustrated in FIG. 2, the rotatable disc 208 may be located at the distal end 218 of the surgical tool 202 and may be adjusted in either of the rotational directions of arrow 245. In other implementations, the rotatable disc 208, or the other movable component, of the surgical tool 202 may be provided in other locations and may move in other ways, including translationally or rotationally about an axis different from the longitudinal axis 209. The rotatable disc 208 may be configured such that the orientation of the tool tip 206 is changed when the orientation of the rotatable disc 208 is adjusted. For example, rotation of the rotatable disc 208 about the longitudinal axis 209 causes a corresponding rotation of the tool tip 206 about the longitudinal axis 209. In the illustrated example of FIG. 2, the rotatable disc 208 also includes a plurality of notches 212 formed in an outer surface of the rotatable disc 208. The notches 212 are separated by a plurality of raised portions 210. The plurality of notches 212 may improve the ability of a user to grip and adjust the rotatable disc 208. In other instances, the rotatable disc 208 may have a knurled surface that may also make the rotatable disc 208 easier to grip and adjust. Other surface textures may be applied to the rotatable disc 208 to improve gripping and adjustment of the rotatable disc 208. In still other implementations, the rotatable disc 208 may have a smooth outer surface.

In some implementations, a surgical procedure may be carried out more efficiently by changing the orientation, e.g., the rotational orientation, of the tool tip 206 and the dynamic component 216 relative to the handle portion 203 or the actuation lever 214, depending on the phase of the procedure and the portion of the patient's eye 10 that is being grasped, cut, or otherwise manipulated. However, in other implementations, for example where the dynamic component 216 includes the Tack Microforceps or similar forceps, as depicted in FIG. 2, a surgical procedure may be more advantageously carried out with the orientation of the tool tip 206 and the dynamic component 216 remaining constant. That is, in some instances, having a rotational orientation of the tool tip 206 fixed relative to the surgical tool 202 may be desirable. Thus, the surgical tool system 200a may include the surgical tool attachment 300a.

The surgical tool attachment 300a is described in more detail below with respect to FIG. 4. The surgical tool attachment 300a may be attached to the surgical tool 202 and positioned such that the surgical tool attachment 300a interferes with and secures the rotatable disc 208 in a selected orientation. The surgical tool attachment 300a may be configured such, when attached to the surgical tool 202, that the surgical tool attachment 300a does not rotate relative to the surgical tool. For example, as shown in FIG. 2 and FIG. 4B, the surgical tool attachment 300a may have a cavity 306 that has a cross-section shape that corresponds to a cross-section shape of the surgical tool 202. In this implementation, the corresponding cross-sectional shapes prevent the surgical tool attachment 300a from rotating relative to the surgical tool 202.

The surgical tool attachment 300a may be coupled to the surgical tool 202 by sliding the surgical tool attachment 300a over a proximal end 220 of the surgical tool 202. The surgical tool attachment 300a may then slide along the surgical tool 202 in the direction of arrow 225 toward the distal end 218 of the surgical tool 202. The surgical tool attachment 300a may then be positioned such that the surgical tool attachment 300a interferes with the rotatable disc 208. For example, the surgical tool attachment 300a may interfere with the rotatable disc 208 by either sliding into one of the plurality of notches 212 or sliding over one of the plurality of raised portions 210, as described in more detail below with respect to FIGS. 4 and 5. In other implementations, the rotatable disc 208 may include a plurality of apertures, and the surgical tool attachment 300a may include a protrusion that is receivable into any of the plurality of apertures to prevent rotation of the rotatable disc 208. Further, other interlocking features formed on the rotatable disc 208 and the surgical tool attachment 300a may be used to prevent rotation of the rotatable disc 208 when the rotatable disc 208 and the surgical tool attachment 300a engage each other.

The surgical tool attachment 300a may also be removed from the surgical tool 202 by sliding the surgical tool attachment 300a along the surgical tool 202 in the direction of arrow 235. The surgical tool attachment 300a may then be fully removed by sliding the surgical tool attachment 300a off of the proximal end 220 of the surgical tool 202. The surgical tool attachment 300a may be removed for cleaning, repair, storage or any other reason between surgical procedures for which the use of the surgical tool attachment 300a is desired.

FIGS. 4A, 4B, 4C, and 4D show different views of the surgical tool attachment 300a. FIG. 4A illustrates the surgical tool attachment 300a includes a body 302. The body 302 has a circular outer cross-sectional shape. In some implementations, the body 302 may be designed to have an outer cross-sectional shape that is similar to a cross-sectional shape of the surgical tool 202 to which the surgical tool attachment 300a may be coupled. However, the surgical attachment tool 300a may have other shapes. For example, in some instances, the outer cross-sectional shape of the surgical tool attachment 300a may be, although not limited to, square, rectangular, triangular, multi-faceted, or a non-uniformed cross-sectional shape, among others.

The surgical tool attachment 300a also includes a tab 304a extending from a first end 314 of the body 302. The tab 304a is located on out outer edge 305 of the first end 314 of the body 302. The surgical tool attachment 300a also includes a plurality of depressions 310a, 310b, and 310c, as shown in FIGS. 4A, 4C, and 4D. The depressions 310a, 310b, and 310c provide for improved gripping of the surgical tool attachment 300a and/or the surgical tool system 200a. In those implementations where the depressions 310a, 310b, and 310c are included, a first hand of a user used to grasp the surgical tool system 200a may experience an ergonomic grip when holding the surgical tool system 200a and, therefore, experience less fatigue due to gripping during a surgical procedure. Although the surgical tool attachment 300a is depicted in FIGS. 4A, 4C, and 4D as having three the depressions (i.e., depressions 310a, 310b, and 310c), the disclosure is not so limited. In some implementations, the surgical tool attachment 300a may have more than three depressions or fewer than three depressions. Further, in other implementations, the body 302 of the surgical tool attachment 300a may include one or more bulges so as to provide tactile feedback to the user. The one or more bulges may be in addition to one or more depressions, such as depressions 310a, 310b, and 310c. In other implementations, the body 302 of the surgical tool attachment 300a may omit the depressions 310a, 310b, and 310c while including one or more bulges.

The surgical tool attachment 300a also include an aperture 312 that extends through the body 302 to prevent pressure and vacuum from building up between the surgical tool attachment 300a and the surgical tool 202, such as when the surgical tool attachment 300a is being attached and/or removed from the surgical tool 202. In some implementations, the aperture 312 may be positioned such that a ventilation passage formed in the surgical tool 202 aligns with the aperture 312, thereby keeping the ventilation passage open and preventing positive or negative pressure from building within the surgical tool 202. As shown in FIG. 4A, the aperture 312 is located within the depression 310a and aligned with the tab 304a. However, the aperture 312 may be positioned at different locations in the surgical tool attachment 300a and continue to function to prevent the generation of positive or negative pressure between the surgical tool attachment 300a and the surgical tool 202.

Referring now to FIG. 4B, the tab 304a is shown positioned on the outer edge 305 of the first end 314 of the body 302. In this position, the tab 304a aligns with one of the plurality of notches 212 or one of the plurality of raised portion 210 of the rotatable disc 208 when the surgical tool attachment 300a is attached to the surgical tool 202, as depicted in FIGS. 1 and 2. In some implementations, the tab 304a may be positioned differently with respect to the body 302 such that the tab 304a interferes or otherwise interacts with the rotatable disc 208 of the surgical tool 202 so as to prevent rotation of the rotatable disc 208.

In the example shown in FIG. 4B, the tab 304a has a semi-circular cross-sectional shape that corresponds to the shape of the notches 212. As a result, the tab 304a is receivable into one or more of the plurality of notches 212 when the surgical tool attachment 300a is attached to the surgical tool 202. In other implementations, the tab 304a may be designed with other cross-sections that conform to a shape of the notches 212 formed in the rotatable disc 208. In other implementations, such as that shown in FIG. 5 and discussed in more detail below, a shape of the tab 304b may be selected such that the tab 304b engages one of the raised portions 210 of the rotatable disc 208 to prevent rotation of the rotatable disc 208 when the surgical tool attachment 300b is attached to the surgical tool 2002.

The surgical tool attachment 300a also includes the cavity 306 that extends longitudinally through the body 302 from the first end 314 to a second end 316. The cavity 306 defines a centerline 320. In some instances, the centerline 320 may align with the longitudinal axis 209. In the example shown in FIG. 4B, the cavity 306 has a cross-sectional shape that corresponds to a hexagonal cross-section of the surgical tool 202 depicted in FIGS. 1 and 2. In some implementations, the cavity 306 may be designed to have other cross-sectional shapes that correspond to the cross-section shape of other instruments, handles, or tools. The cavity 306 may be designed to allow for the surgical tool attachment 300a to be coupled to the surgical tool 202 by aligning the cavity 306 with the proximal end 220 of the surgical tool 202 and sliding the surgical tool attachment 300a along the surgical tool 202 in the direction of arrow 225, as described above in reference to FIG. 2.

The surgical tool attachment 300a also includes a slot 308 that extends lengthwise through the body 302 from the first end 314 to the second end 316. In the illustrated example, the slot 308 is located 180° offset about the centerline 320 from the tab 304a, extends from an outer surface 318 of the body 302, and intersects with the cavity 306. Thus, the slot 308 extends radially outwards from the cavity 306 relative to the centerline 320 and extends entirely through the body 302. In some implementations, the slot 308 may extend only partially along a length 325 of the surgical tool attachment 300a. In other implementations, the slot 308 may extend along an entirety of the length 325. In some instances, the slot 308 may be sized so as to ensure that the surgical tool attachment 300a does not interfere with actuation of an actuation component or mechanism operable to actuate the dynamic component 216. For example, as depicted in FIG. 2, the slot 308 provides clearance for the actuation lever 214 to be depressed without interfering with the body 302 of the surgical tool attachment 300a.

FIGS. 4D and 4C depict top and bottom views, respectively, of the surgical tool attachment 300a.

Figure 3:
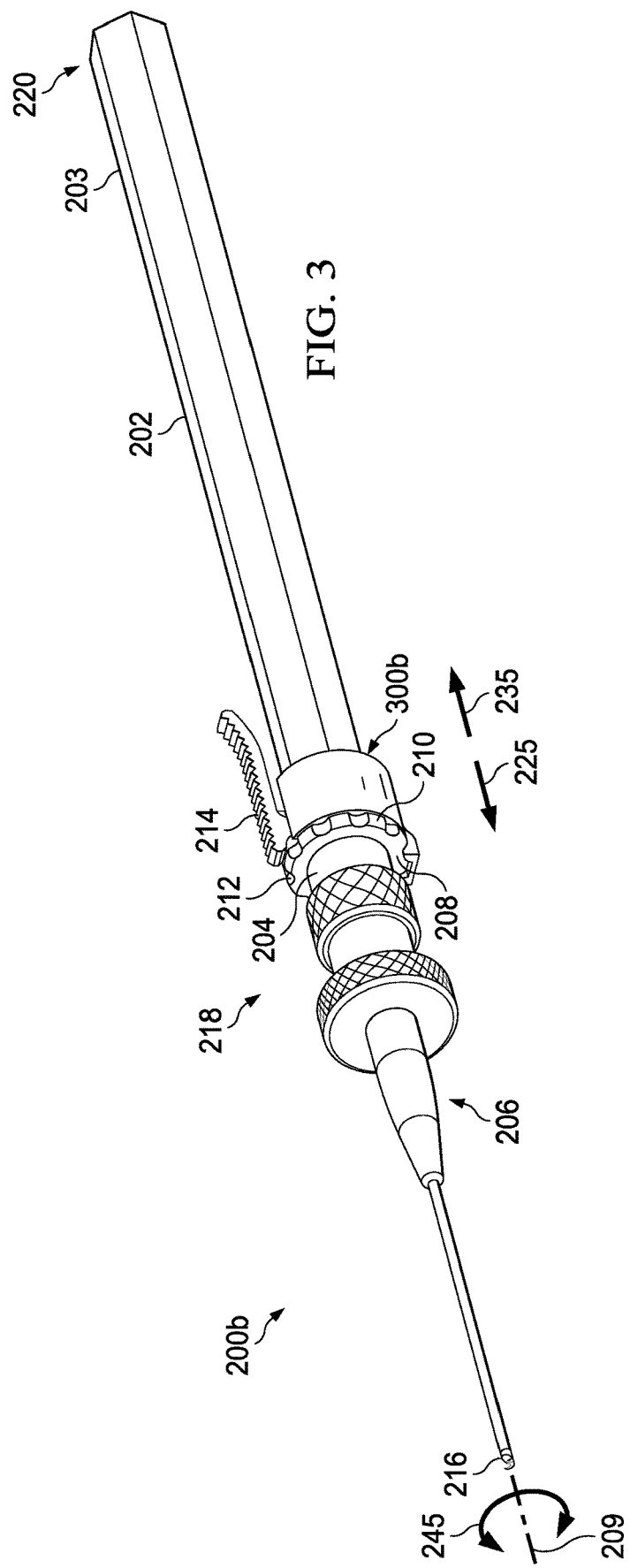
FIG. 3 is a perspective view of an example surgical tool system with another example surgical tool attachment and a surgical tool similar to a GRIESHABER SUTHERLAND NG handle.

FIG. 3 illustrates another example surgical tool system 200b with an example surgical tool attachment 300b and a surgical tool 202. The surgical tool 202 may be similar to the surgical tool 202 described above in the context of FIG. 2. Consequently, descriptions of the various parts of the surgical tool 202 provided in the context of the surgical tool 202 shown in FIG. 2 are applicable to the like components of the surgical tool 202 shown in FIG. 3. Therefore, further description of these components is omitted. In some implementations, the surgical tool may be a GRIESHABER SUTHERLAND NG handle described previously. However, in other implementations, the surgical tool 202 may be any other type of surgical tool, such as one of those described herein or other surgical tools. The surgical tool system 200b depicted in FIG. 3 includes components similar to those described above in the context of the surgical tool system 200a. Here, though, the surgical tool system 200b includes a surgical tool attachment 300b rather than the surgical tool attachment 300a that is depicted in FIG. 2. The surgical tool attachment 300b is described in detail below with reference to FIGS. 5A-5C.

Figure 5A:
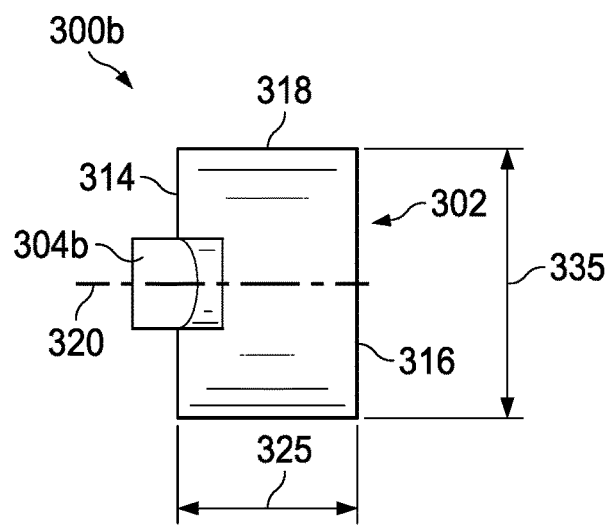
FIGS. 5A, 5B, and 5C are various views of another example surgical tool attachment.
Figure 5B:
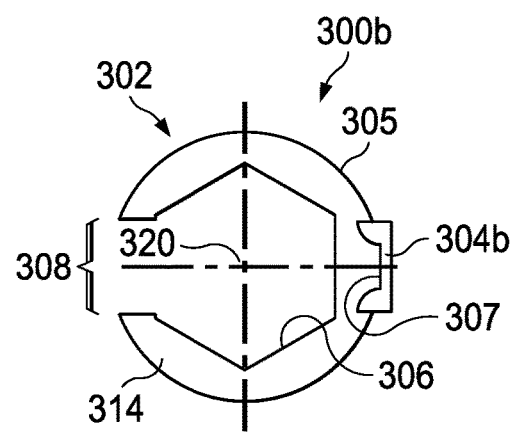
Figure 5C:
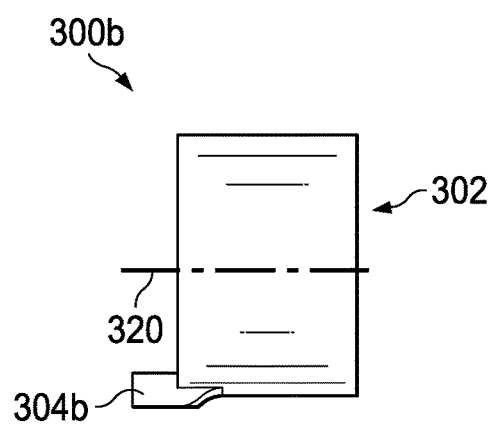

FIGS. 5A, 5B, and 5C show different views of the surgical tool attachment 300b. The surgical tool attachment 300b may be similar to the surgical tool attachment 300a. As depicted in FIG. 5A, the surgical tool attachment 300b includes a body 302 that has a circular outer cross-sectional shape. In some instances, the body 302 may have an outer cross-sectional shape that is similar to a cross-sectional shape of the surgical tool 202 to which the surgical tool attachment 300b attaches. In the illustrated example, the surgical tool attachment 300b omits depressions (such as the depressions 310a, 310b, and 310c formed in the body 302 of the surgical tool attachment 300a) and an aperture formed through the body 302 (such as the aperture 312 formed in the surgical tool attachment 300a shown in FIG. 4A). However, in other implementations, the surgical tool attachment 300b may include these features similarly to the surgical tool 300a described above. Although the body 302 of the surgical tool attachment 300b is shown has having a length 325 that is less than a length 325 of the body 302 of the surgical tool attachment 300a, the length 325 of the body 302 of the surgical tool attachments 300a and 300b may vary and still remain within the scope of this disclosure. For example, the body 302 may be designed to have the length 325 that is larger than a width 335 or the body 302 may be designed to have the width 335 that is larger than the length 325.

The surgical tool attachment 300b includes a tab 304b on a first end 314 of the body 302. The tab 304b may be arranged on the body 302 in a manner similar to that of the tab 304a, as described above with reference to FIGS. 4A and 4B. As depicted in FIG. 5B, the surgical tool attachment 300b includes a cavity 306 and a slot 308, which are similar to those described above with respect to the surgical tool attachment 300a. The tab 304b is shown positioned on the outer edge 305 of the first end 314 of the body 302. In some implementations, this positioning of the tab 304b allows the tab 304b to align with the plurality of raised portions 210 or the plurality of notches 212 of the rotatable disc 208 when the surgical tool attachment 300b is coupled to the surgical tool 202, as depicted in FIGS. 1 and 3. In some implementations, the tab 304b may be positioned or configured differently with respect to the body 302 such that the tab 304b interferes or otherwise interacts with one or more features of the rotatable disc 208 other than the plurality of notches 212 and raised portions 210. For example, as explained above, the rotatable disc 208 may include a plurality of apertures, and the surgical tool attachment 300b may include a protrusion that is receivable into any of the plurality of apertures to prevent rotation of the rotatable disc 208. Further, other interlocking features formed on the rotatable disc 208 and the surgical tool attachment 300b may be used to prevent rotation of the rotatable disc 208 when the rotatable disc 208 and the surgical tool attachment 300b engage each other.

As depicted in FIG. 5B, the tab 304b has a generally "C-shaped" cross-section that defines a channel 307. Opposite ends 309 of the tab 304b have a curved shape that conforms to the shape of the notches 212 formed in the rotatable disc 308. The channel 307 is sized to accept a raised portion 210 of the rotatable disc 208. Thus, in use, when the surgical tool attachment 300b is moved into engagement with the rotatable disc 208, one of the raised portions 210 is received within the channel 307 of the tab 304b and the ends 390 of the tab 304b are received into corresponding notches 212 formed in the rotatable disc 208 that are on opposite sides of the raised portion 210 received into the channel 307. This engagement between the tab 304b and the rotatable disc 208 prevents the rotatable disc 208 from being able to rotate relative to the surgical tool 202, thereby keeping the tool tip 206 in a fixed position about the longitudinal axis 209 relative to the surgical tool 202. In other implementations, the tab 304b may be designed with other cross-sectional shapes. For example, the tab 304b may have a cross-sectional shape that is the same or similar to that of the tab 304a, depicted and described above in reference to FIG. 4B.

FIG. 5C depicts a bottom view of the surgical tool attachment 300b. As shown in further detail, the surgical tool attachment 300b shows the tab 304b located on the first end 314 of the body 302.

Although the example surgical tool systems 200a and 200b are disclosed as having the respective surgical tool attachments 300a and 300b being removable from the surgical tools 202, other configurations are within the scope of the disclosure. For example, in some implementations, the surgical tool attachment 300a or 300b may be integral to and retained on the surgical tool 202. Thus, in operation, a user may slide the surgical tool attachment distally so that the surgical tool attachment engages the rotatable disc 208, thereby preventing rotation of the tool tip 206 relative to the surgical tool 202. Conversely, a user may slide the integral surgical tool attachment proximally to disengage the rotatable disc 208, thereby permitting the tool tip 206 to rotate relative to the surgical tool 202.

Figure 6:
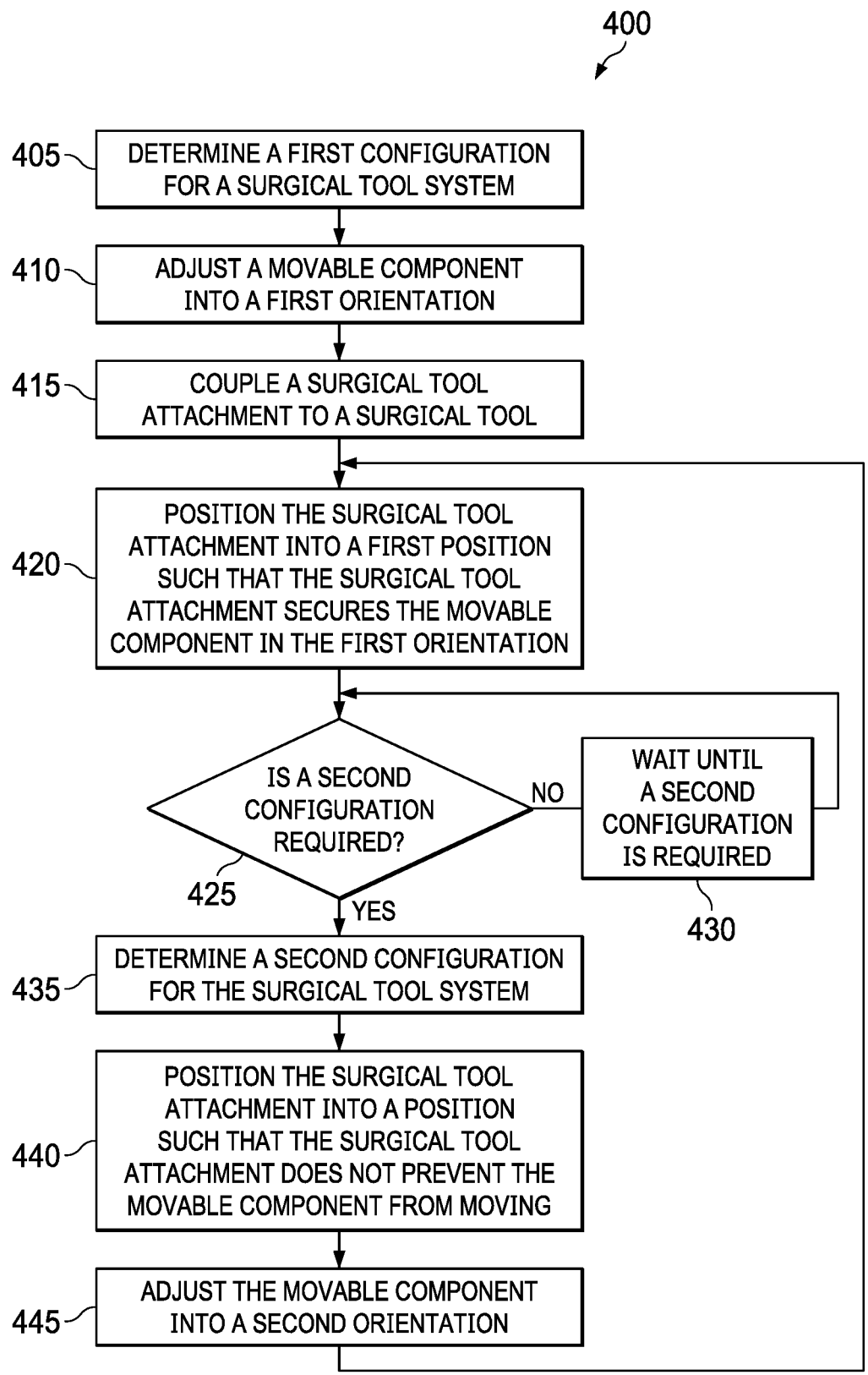
FIG. 6 is a flowchart of an example method of configuring a surgical tool system.

FIG. 6 is a flowchart of an example method 400 of configuring a surgical tool system. In some instances, the method 400 may be accomplished by one or more of the systems described herein, such as the surgical tool systems 200a or 200b. Additionally, actions described above with respect to components of the systems encompassed by the present disclosure and as described herein may be performed in the method 400, even if not expressly described in connection with the flow chart.

At step 405, a first configuration for a surgical tool system is determined. The surgical tool system may include a surgical tool and a surgical tool attachment. The first configuration may be defined by an orientation of a movable component of the surgical tool system relative to the surgical tool and a position of the surgical tool attachment with respect to the surgical tool. For example, a rotational orientation of the rotatable disc 208 relative to the surgical tool 202 and a longitudinal position of the surgical tool attachment 300a, 300b relative to the surgical tool 202 may define a first configuration of a surgical tool system. The first configuration of the surgical tool system may be determined such that the surgical tool system may be advantageously used during a surgical procedure. For example, the first configuration of the surgical tool system may result in a dynamic component of the surgical tool system being secured in a defined orientation relative to the surgical tool such that the surgical procedure may be efficiently performed.

At step 410, the movable component of the surgical tool is adjusted into a first orientation that corresponds to the first configuration of the surgical tool system. The surgical tool and the movable component may be designed to allow for a plurality of different orientations. For example, the surgical tool systems 200a and 200b and the rotatable disc 208 allow for a plurality of rotational orientations of the tool tip 206 and dynamic component 216 thereof relative to the surgical tool 202.

At step 415, the surgical tool attachment is coupled to the surgical tool. In some instances, the surgical tool attachment may be similar to the surgical tool attachments 300a and 300b, and the surgical tool may be similar to the surgical tool 202. In some instances, coupling the surgical tool attachment to the surgical tool may include aligning the surgical tool attachment with a distal end of the surgical tool, placing the surgical tool attachment in contact with the surgical tool, and sliding the surgical tool attachment toward a proximal end of the surgical tool. The surgical tool attachment may define a cavity. The cavity may be aligned with the distal end of the surgical tool, and an inner surface of the cavity may be in contact with an outer surface of the surgical tool as the surgical tool attachment slides along the surgical tool. In some implementations, step 415 may be omitted as the surgical tool attachment may be integral to the surgical tool.

At step 420, the surgical tool attachment is positioned into a first position such that the surgical tool attachment secures the movable component in the first orientation relative to the surgical tool. The surgical tool system may be considered in the first configuration when the surgical tool attachment is disposed in the first position. In some instances, positioning the surgical tool attachment may include positioning the surgical tool attachment at the proximal end of the surgical tool nearest the movable component, aligning a tab on the surgical tool attachment with a feature formed on the moveable component (e.g., a notch formed on an edge of the movable component), and inserting the tab into the notch. For example, the tab may be similar to the tabs 304a or 304b and may be inserted into a single notch or into multiple notches and on opposing sides of a raised portion of the movable component. The surgical tool attachment may prevent the movable component from moving out of the first orientation and may secure the surgical tool system in the first configuration.

At step 425, the surgical tool system may remain in the first configuration and may be used to carry out a surgical procedure. In some instances, a second configuration of the surgical tool system may be desired. For example, the second configuration of the surgical tool system may be better suited for efficient completion of a phase of the surgical procedure. If a second configuration is desired, the method 400 advances to step 435. If a second configuration is not required, the method 400 advances to step 430. At step 430, the surgical tool system may remain in the first configuration until a second configuration may be desired.

At step 435, a second configuration of the surgical tool system is determined. Determining the second configuration may be done in a similar fashion to how the first configuration was determined in step 405. The second configuration may be defined by the movable component being in a second orientation and/or the surgical tool attachment being in a second position.

At step 440, the surgical tool attachment is positioned into an intermediate position such that the surgical tool attachment does not prevent the movable component from moving. For example, in some implementations, the surgical tool attachment may be positioned such that the tab of the surgical tool attachment is removed from the notch of the movable component or otherwise taken out of contact with the movable component. Positioning the surgical tool attachment into the intermediate position may allow for the movable component to move freely relative to the surgical tool and be adjusted relative thereto as needed.

At step 445, the movable component is adjusted into the second orientation that corresponds to the second configuration of the surgical tool system. As described above with respect to step 410, the surgical tool and the movable component may be designed to allow for a plurality of orientations. After the movable component is adjusted into the second orientation, the method 400 is returned to step 420.

Step 420 may be repeated as many times as desired to change the configuration of the surgical tool system from one configuration of the surgical tool system to the another configuration. During this pass through the method 400, the surgical tool attachment may be positioned in a second position that corresponds to the second configuration and secures the movable component in the second orientation. Steps 425, 430, 435, and 445 may also each be repeated as many times as necessary to change the configuration of the surgical tool system.

Although the method 400 illustrates an example method for configuring a surgical tool system, other methods for configuring the surgical tool system may include fewer, additional, or a different arrangement of operations. For example, although not depicted in FIG. 6, the method 400 may further include locating the surgical tool that is part of the surgical tool system in a patient's eye.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A surgical tool system comprising:
   a surgical tool comprising:
      a handle portion configured to be grasped by a hand of a user;
      a ventilation passage formed in the surgical tool;
      at least one movable component; and
      at least one actuation component; and
   a surgical tool attachment configured to be coupled to the surgical tool, the surgical tool attachment comprising:
      a body comprising:
         a tab extending from a first end of the body and operable to interfere with the at least one movable component of the surgical tool;
         a cavity extending longitudinally through the body and configured to slidably receive the surgical tool, wherein the cavity comprises a non-round cross-sectional shape that corresponds to a complimentary non-round cross-sectional shape of the surgical tool; and
         a slot extending radially outwards from the cavity through an entirety of a side of the body and extending at least partially along a length of the body so as to not interfere with the at least one actuation component of the surgical tool;
      wherein the surgical tool attachment further comprises an aperture formed in the body and extending from the cavity to an exterior of the body, wherein the aperture aligns with the ventilation passage to prevent positive or negative pressure between the surgical tool attachment and the surgical tool when the surgical tool attachment is being attached and/or removed from the surgical tool.

2. The surgical tool system of claim 1, wherein the surgical tool attachment is integrated into the surgical tool.

3. The surgical tool system of claim 1, wherein the tab is disposed on an outer edge of the body.

4. The surgical tool system of claim 1, wherein the cross-sectional shape of the cavity is hexagonal.

5. The surgical tool system of claim 1, wherein the surgical tool attachment further comprises at least one depression formed in an exterior surface of the body, the exterior surface of the body forming an ergonomic gripping surface to the hand of the user.

6. The surgical tool system of claim 1, wherein the at least one movable component comprises a plurality of notches, and
   wherein the tab comprises a cross-sectional shape that corresponds to a cross-sectional shape of the notches, and
   wherein the tab is configured to be insertable into at least one of the notches so as to secure the at least one movable component in an orientation with respect to the surgical tool.

7. The surgical tool system of claim 1, wherein the at least one movable component comprises a plurality of raised portions,
   wherein the tab has a cross-sectional shape that defines a channel that is configured to receive at least one of the raised portions of the at least one movable components so as to secure the at least one movable component in an orientation with respect to the surgical tool.

\* \* \* \* \*